(12) United States Patent
Gras et al.

(10) Patent No.: US 6,479,613 B2
(45) Date of Patent: Nov. 12, 2002

(54) PROCESS FOR THE PREPARATION OF POLYADDITION PRODUCTS CONTAINING URETDIONE GROUPS, AND THEIR USE IN POLYURETHANE COATING SYSTEMS

(75) Inventors: Rainer Gras, Bochum (DE); Siegfried Brandt, Haltern (DE); Klaus Behrendt, Herne (DE); Silvia Herda, Herne (DE)

(73) Assignee: Dugussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 08/667,278

(22) Filed: Jun. 20, 1996

(65) Prior Publication Data

US 2002/0062000 A1 May 23, 2002

Related U.S. Application Data

(63) Continuation of application No. 08/362,862, filed on Dec. 23, 1994, now abandoned.

(30) Foreign Application Priority Data

Feb. 28, 1994 (DE) ........................................ 44 06 445

(51) Int. Cl.$^7$ ................................................ C08G 18/79
(52) U.S. Cl. ........................................ 528/73; 548/951
(58) Field of Search ............................ 528/73; 548/951

(56) References Cited

U.S. PATENT DOCUMENTS

4,413,079 A * 11/1983 Disteldorf et al. .......... 524/169
4,483,798 A * 11/1984 Disteldorf .................... 528/59
4,595,709 A * 6/1986 Reische ........................ 521/79

FOREIGN PATENT DOCUMENTS

| BE | 571 279 | 10/1958 |
| EP | 0 033 927 | 8/1981 |
| EP | 0 045 996 | 2/1982 |
| EP | 0 519 734 | 12/1992 |
| FR | 2 298 566 | 8/1976 |

* cited by examiner

*Primary Examiner*—Rachel Gorr
(74) *Attorney, Agent, or Firm*—Oblon, Spivak, McClelland, Maier & Neustadt, P.C.

(57) ABSTRACT

The invention relates to a process for the preparation of polyaddition products containing uretdione groups, prepared from a polyisocyanate-uretdione having at least two free isocyanate groups, diols and, if desired, monoalcohols or monoamines, in which the polyaddition products containing uretdione groups are prepared by a solvent-free and continuous procedure which is carried out in an intensive kneading apparatus/extruder. The invention also relates to the use of polyaddition products containing uretdione groups for PUR powder coatings and for solvent-containing, one-component stoving enamels.

19 Claims, No Drawings

PROCESS FOR THE PREPARATION OF POLYADDITION PRODUCTS CONTAINING URETDIONE GROUPS, AND THEIR USE IN POLYURETHANE COATING SYSTEMS

This application is a continuation of application Ser. No. 08/362,862, filed on Dec. 23, 1994, now abandoned.

BACKGROUND OF THE INVENTION

1. Field of the Invention

The present invention relates to a novel, simple process for the preparation of polyisocyanates containing uretdione groups and to their use in light-stable and weather-stable polyurethane (PUR) coating systems, especially in PUR powder coatings.

2. Discussion of the Background

DE-A 30 30 572 presents a process for the preparation of polyaddition products which contain uretdione groups, and the products prepared accordingly. These are reaction products of the isocyanurate-free uretdione (UD) of 3-isocyanatomethyl-3,5,5-trimethylcyclohexyl isocyanate (isophorone diisocyanate, IPDI)—which can be prepared according to DE-A 30 30 513 or DE-A 37 39 549—with diols and, if desired, monoalcohols or monoamines. The reaction can be carried out in bulk or else in the presence of appropriate solvents. However, so far, in practice, this class of crosslinking agent has been produced in economically significant, saleable quantities only in a suitable solvent under mild conditions, at about 60°C., so as to avoid thermal ring cleavage during the synthesis. Preparation in bulk (i.e. in the absence of solvent) has not previously gone beyond the laboratory scale, since the viscosity reaches unmanageable levels during the reaction as a function of the molecular mass of the crosslinking agent. While DE-A 3030572 indicates that increasing the reaction temperature can operate as a means of controlling the reaction viscosity this measure is somewhat limited since higher temperatures can lead to detrimental effects on the reaction products. The industrial implementation of the solvent-free preparation of polyaddition products containing uretdione groups has previously been without success, despite the numerous corresponding attempts to solve this problem. Production in solvent not only has the disadvantage that the solvent(s) must be removed again subsequently, but also that it requires long reaction times and complex, reaction products are freed from the solvent in vacuo at about 120° C. using thin-film evaporators, filmtruders or extruders. This makes the process very costly.

Thus, a method is needed for the bulk preparation of polyisocyanates containing uretdione groups.

SUMMARY OF THE PREFERRED INVENTION

Accordingly, one object of the present invention is to a simple process for the production of polyisocyanates containing uretdione groups, which is solvent free.

A further object of the present invention is to provide a process for the bulk production of polyisocyanate containing uretdione groups which maintains a manageable viscosity throughout the process.

A further object of the present invention is to provide polyurethane coating systems containing bulk prepared polyisocyanates having uretdione groups.

Surprisingly it has been found that the reaction of polyisocyanate-uretdione with diols and, if desired, with monoalcohols or monoamines can be carried out continuously in bulk, in other words without solvent, in an intensive mixer, provided that certain process conditions are observed.

DETAILED DESCRIPTION OF THE PREFERRED EMBODIMENTS

The invention therefore relates to a process for the preparation of polyaddition products containing uretdione groups and based on polyisocyanate-uretdione having at least two free isocyanate groups, on diols and, if desired, on monoalcohols or monoamines, which process is characterized in that the polyaddition products containing uretdione groups are prepared by a solvent-free and continuous procedure.

The present process relies on the ability to continuously heat the reaction products for short periods in an intensive kneading apparatus, such as a single- or multi-screw kneading apparatus, preferably in a twin-screw extruder, at temperatures which are unusually high for polyisocyanates containing uretdione groups, but are necessary for the solvent-free preparation.

These unusually high synthesis temperatures can exceed 120° C., and range up to 190° C. The reason that such temperatures are considered unusually high is that these temperatures are already well within the range in which uretdiones unblock, so that high free isocyanate contents or uncontrolled reaction procedures would be expected. However, this was not the case.

The temperatures in the intensive kneading apparatus or twin-screw extruder must be sufficient to provide reaction between the reactants and to maintain a manageable viscosity, with these temperatures ranging up to 190° C., preferably up to 180° C., most preferably up to 170° C.

In the present process the brief exposure to heat must be sufficient to allow the reactants to be mixed homogeneously and to react to at least near completion (>95%). Controlled cooling is then carried out in accordance with the establishment of equilibrium, and, if desired, conversion is completed.

By appropriate equipping of the mixing chambers and/or the composition of the screw geometry, the intensive kneading apparatus renders possible intensive, rapid mixing and highly viscous product streams coupled with intensive heat exchange. Additionally, uniform flow in the longitudinal direction with a residence time which is as uniform as possible is also obtained. Furthermore, it must be possible to set different temperatures in the individual housings or sections of the device.

The reactants are metered to the intensive kneading apparatus in separate streams and/or as one or more streams containing more than one reactant. One such mixed reactant stream would include a combination of diols, monoalcohols, monoamines, catalysts and/or other conventional coating additives, such as levelling agents and stabilizers. Another example of a mixed stream would include a polyisocyanate-UD and those components which are inert towards isocyanate groups: catalysts and, correspondingly, coating additives as mentioned above.

The input of the product streams into the kneading apparatus can varied in sequence and offset in terms of time. The controlled cooling step which occurs after kneading can be performed using: tube bundles, pipe coils, cooling rolls, air conveyors and, preferably metal conveyor belts. Most preferably, the cooling means should allow for the setting of individual temperature zones. If desired the controlled cooling in the reaction section can be integrated in the form of a multi-housing apparatus, as in the case of extruders or Conterna machines.

The final stages of processing are initiated, depending on the viscosity of the product leaving the screw extruder and/or the post-reaction zone, first by further cooling—using controlled cooling devices as mentioned above—to a temperature which is sufficient for subsequent bagfilling/containment with comminution being carried out before bag-filling. During cooling, at an appropriate point, the product (which is produced preferably in strip form) can be pre-impressed in order to prepare for and facilitate subsequent comminution to the desired particle size or granule form, using roll-type crushers, pin mills, hammer mills or similar apparatus, and to reduce the amount of dust obtained. If a bed of coded rolls is used, this pre-impression can be combined with cooling and the dust collected afterward can be recycled directly and re-incorporated into the product.

Surprisingly, with respect to their physical and chemical characteristics and their technological properties, the crosslinking agents prepared according to the present invention are indistinguishable (within the margin of experimental error) from the same crosslinking agents prepared in conventional solvent based processes under much different conditions.

As starting compounds for use in the process of the present invention, it is possible to use uretdiones of diisocyanates, uretdiones prepared from two different diisocyanates, so-called mixed dimers (uretdiones) of mixtures of uretdiones or mixtures thereof. The diisocyanates suitable for the process of the present invention include aliphatic, (cyclo)aliphatic and araliphatic diisocyanates such as those described in Houben-Weyl, Methoden der Organischen Chemie [Methods of Organic Chemistry], Volume 14/2, pp. 61–70 or the article by W. Siefken in Justus Liebigs Annalen der Chemie 562, pp. 75–136. Preferred diisocyanates include 1,4-tetramethylene diisocyanate, 1,6-hexamethylene diisocyanate (HDI), methylpentamethylene diisocyanate, 2,2,4 or (2,4,4)-tri-methylhexamethylene 1,6-diisocyanate (TMDI), cyclohexane 1,3- and 1,4-diisocyanate, 3-isocyanatomethyl-3,5,5-trimethyl-cyclohexyl isocyanate [isophorone diisocyanate (IPDI)], hexahydrodurene diisocyanate, 4,4'-diisocyanatodicyclohexylmethane (HMDI), m- or p-tetramethylxylylene diisocyanate (TMXDI) and hexahydroxylylene 1,4- and 1,3-diisocyanate. The uretdione of isophorone diisocyanate is particularly preferred. The diisocyanatouretdiones can be prepared using conventional isocyanate methods.

The polyaddition products containing uretdione groups, are prepared using diols. Examples of suitable dihydric alcohols include ethylene glycol (E), propylene glycols, such as 1,2- and 1,3-propanediol, 2-methylpropane-1,3-diol (NPG), 2,2-dimethylpropane-1,3-diol (MPG), butane-1,4-diol (B), diethylene glycol (DEG), hexanediol (HD), octane-1,8-diol, 3-methylpentanediol (Pm), 2,2,4 (or 2,4,4)-trimethylhexanediol (TMH-d), dodecane-1,12-diol, octadecane-1,18-diol, neopentylglycol hydroxypivalate (Eg), and trans- and cis-1,4-cyclohexanedimethanol (DMC).

In the preparation of the polyaddition products containing uretdione groups, the method of the present invention reacts a polyisocyanate-uretdione and diol, in amounts sufficient to provide OH/NCO ratio of from 0.5:1 to 1.5:1. When the OH/NCO ratio results in excess free NCO groups, these NCO groups can, if desired be reacted, in whole or in part, with monoalcohols or monoamines.

Suitable monohydric alcohols include methanol (M), ethanol (Et), n- or isopropanol, n-butanol, 2-ethylhexanol (EH), n-decanol, and cyclohexanol. Suitable monoamines include n-propylamine, n-butylamine, n-hexylamine, dibutylamine (DBA) and dicyclohexylamine.

To accelerate the isocyanate polyaddition reaction, catalysts can also be employed if desired. Suitable catalysts include any conventional catalysts used in isocyanate chemistry, such as organic tin(II) and tin(IV) compounds, and zinc octanoate. Preferred tin(II) and tin(IV) compounds include tin(II) acetate, tin(II) octanoate, tin(II) laurate, dibutyltin dilaurate (DBTL), dibutyltin diacetate, dibutyltin maleate or dioctyltin diacetate. The catalyst concentration, if catalyst is used, is between 0.01 and 2% by weight, preferably between 0.05 and 1% by weight based on the expected theoretically yield of end product.

The present invention also relates to the use of the polyaddition products containing uretdione groups, prepared by the method of the present invention, for the formulation of storage-stable, heat-curable PUR powder coatings and solvent-containing, one-component PUR stoving enamels.

Suitable co-reactants for PUR powder coatings are compounds which contain one or more functional groups which react with isocyanate groups during the curing process as a function of temperature and time, such as hydroxyl, carboxyl, mercapto, amino, urethane and (thio)urea groups. Polymers which can be employed include both condensation polymers and addition polymers.

Preferred polymeric components include polyethers, polythioethers, polyacetals, polyesteramides, epoxy resins containing hydroxyl groups in the molecule, amino resins and their modification products with polyfunctional alcohols, polyazomethines, polyurethanes, polysulphonamides, melamine derivatives, cellulose esters and ethers, partially hydrolysed homo- and copolymers of vinyl esters, polyesters and acrylate resins, with polyester and acrylate resins being most preferred.

The preferred hydroxyl group-containing polyesters which can be used have an OH functionality of from 2.5 to 5, preferably from 3 to 4.2, a number average molecular weight of from 1,800 to 5,000, preferably from 2,300 to 4,500, an OH number of from 25 to 180 mg of KOH/g, preferably from 30 to 140 mg of KOH/g, a viscosity at 160° C. of <80,000 mPa·s, preferably <60,000 mpa·s, most preferably <40,000 mPa·s, and a melting point of from 70° C. and 1200° C., preferably from 75° C. to 100° C.

Carboxylic acids which are preferred for the preparation of the polyesters include aliphatic, cycloaliphatic, aromatic or heterocyclic acids or combinations thereof and may, if desired, be substituted by one or more halogen atoms or unsaturated or both and their esters or anhydrides. Suitable carboxylic acids include succinic, adipic (AS), suberic, azelaic, Bebacic, phthalic, terephthalic (Ts), isophthalic (Is), trimellitic, pyromellitic, tetrahydrophthalic, hexahydrophthalic, hexahydroterephthalic, di- and tetrachloraphthalic, endomethylenetetrahydrophthalic, glutaric, maleic and fumaric acids and—where accessible—their anhydrides, dimethyl terephthalate (DMT), bisglycol terephthalate and also cyclic monocarboxylic acids such as benzoic acid, p-tert-butylbenzoic acid or hexahydrobenzoic acid.

Examples of suitable polyhydric alcohols include ethylene glycol, 1,2-propylene glycol and 1,3-propylene glycol, 1,4-butylene glycol and 2,3-butylene glycol, di-β-hydroxyethylbutanediol, hexane-1,6-diol, octane-1,8-diol, neopentylglycol, cyclohexanediol, 1,4-bis(hydroxymethyl) cyclohexane, 2,2-bis(4-hydroxycyclohexyl)propane, 2,2-bis [(4-(β-hydroxyethoxy)phenyl]propane, 2-methylpropane-1, 3-diol, 3-methylpentane-1,5-diol, 2,2,4(or 2,4,4)-trimethylhexane-1,6-diol, glycerol, trimethylolpropane, trimethylolethane, hexane-1,2,6-triol, butane-1,2,4-triol, tris (β-hydroxyethyl) isocyanurate, pentaerythritol, mannitol, sorbitol, diethylene glycol, triethylene glycol, tetraethylene glycol, dipropylene xylylene glycol and neopentylglycol hydroxypivalate.

Mono- and polyesters of lactones, such as ε-caprolactone, or hydroxycarboxylic acids, such as hydroxypivalic acid, w-hydroxydecanoic acid, and ω-hydroxycaproic acid can also be employed. Also suitable are polyesters of the above-mentioned polycarboxylic acids or their esters or anhydrides with polyphenols, such as hydroquinone, bisphenol A, 4,4'-dihydroxybiphenyl or bis (4-hydroxyphenyl)sulphone; polyesters of carbonic acid obtainable from hydroquinone, diphenylolpropane, p-xylylene glycol, ethylene glycol, butanediol or hexane-1,6-diol and other polyols by conventional condensation reactions with carbonate producing reagents such as phosgene or diethyl or diphenyl carbonate, or from cyclic carbonates such as glycol carbonate or vinylidene carbonate, by conventional polymerization procedures. Further compounds which can be employed are polyesters of silicic acid, polyesters of phosphoric acid, such as those from methane-, ethane-, β-chloroethane-, benzene- or styrenephosphoric acid, or the corresponding phosphoryl chlorides or phosphoric esters, and polyalcohols, or polyphenols of the type mentioned above; polyesters of boric acid; polysiloxanes, such as the products obtained by hydrolysis of dialkyldichlorosilanes with water followed by treatment with polyalcohols, and the products obtained by addition reaction of polysiloxane dihydrides with functionalized olefins, such as allyl alcohol or acrylic acid.

Other preferred polyesters include the reaction products of polycarboxylic acids with glycidyl compounds, as described, for example, in DE-A 24 10 513. Examples of glycidyl compounds which can be used are esters of 2,3-epoxy-1-propanol with monobasic acids having from 4 to 18 carbon atoms (such as glycidyl palpitate, glycidyl laurate and glycidyl stearate) or alkylene oxides having from 4 to 18 carbon atoms, such as glycidyl ether.

The dicarboxylic acids which can be used in this process include all those polycarboxylic acids listed below under II; it is also possible to employ monocarboxylic acids, which are listed under III by way of example.

Other preferred components are monomeric esters, such as bis-hydroxy(alcohol) esters of dicarboxylic acids, esters of monocarboxylic acids with polyols having a functionality of more than two, and oligoesters which can be prepared by condensation reactions from the raw materials which are customary in paint chemistry. Examples of such customary materials include:

I. alcohols having 2 to 24, preferably 2 to 10, carbon atoms and 2 to 6 OH groups which are attached to nonaromatic carbon atoms, such as ethylene glycol, propylene glycol, diethylene glycol, dipropylene glycol, butanediols, neopentyl glycol, hexanediols, hexanetriols, perhydrobisphenol, dimethylolcyclohexane, glycerol, trimethylolethane, trimethylolpropane, pentaerythritol, dipentaerythritol and mannitol;

II. di- and polycarboxylic acids having 4 to 36 carbon atoms and 2 to 4 carboxyl groups and esterifiable derivatives thereof, such as anhydrides and esters, including phthalic acid (anhydride), isophthalic acid, terephthalic acid, alkyltetrahydrophthalic acid, endomethylenetetrahydrophthalic anhydride, adipic acid, succinic acid, maleic acid, fumaric acid, dimeric fatty acids, trimellitic acid, pyromellitic acid and azelaic acid;

III. monocarboxylic acids having 6 to 24 carbon atoms, such as caprylic acid, 2-ethylhexanoic acid, benzoic acid, p-tert-butylbenzoic acid, hexahydro-benzoic acid, mixtures of monocarboxylic acids from natural oils and fats, such as coconut fatty acid, soya-oil fatty acid, castor oil fatty acid, hydrogenated and isomerized fatty acids, such as "Konjuvandol fatty acid and mixtures thereof; it is also possible to use fatty acid glycerides and to react them by transesterification and/or dehydration;

IV. monohydric alcohols having 1 to 18 carbon atoms, such as methanol, ethanol, isopropanol, cyclohexanol, benzyl alcohol, isodecanol, nonanol, octanol and oleyl alcohol.

The polyesters can be obtained in a conventional manner by condensation in an inert gas atmosphere at temperatures of from 100 to 260° C., preferably from 130 to 220° C., in the melt or in an azeotropic procedure, as described in, for example, Methoden der Organischen Chemie [Methods of Organic Chemistry] (Houben-Weyl), volume 14/2, 1–5, 21, 23, 40, 44, Georg Thieme Verlag, Stuttgart, 1963 or in C. R. Martens, Alkyd Resins, 51–59, Reinhold Plastics Appl. Series, Reinhold Publishing Comp., New York, 1961.

Preferred acrylate resins for possible use as OH components are homo- or copolymers of monomers such as the following: esters of acrylic acid and methacrylic acid with dihydric, saturated, aliphatic alcohols having 2 to 4 carbon atoms, such as 2-hydroxyethyl acrylate, 2-hydroxypropyl acrylate, 4-hydroxybutyl acrylate and the corresponding methacrylates; allyl acrylates and methacrylates having 1 to 18 carbon atoms in the alcohol component, such as methyl acrylate, ethyl acrylate, propyl acrylate, isopropyl acrylate, n-butyl acrylate, tert-butyl acrylate, 2-ethylhexyl acrylate, stearyl acrylate and the corresponding methacrylates; cyclohexyl acrylate and methacrylate; acrylonitrile and methacrylo-nitrile, acrylamide and methacrylamide; and N-methoxy-methyl(meth)acrylamide.

Particularly preferred acrylate resins are copolymers of
a. from 0 to 50% by weight of esters of acrylic or methacrylic acid with dihydric or polyhydric alcohols, such as 1,4-butanediol monoacrylate, hydroxypropyl (meth)acrylate; and also vinylglycol, vinylthioethanol, allyl alcohol and 1,4-butanediol monovinyl ether;
b. from 5 to 95% by weight of esters of acrylic acid or methacrylic acid with monohydric alcohols containing from 1 to 12 carbon atoms, such as methyl methacrylate, ethyl acrylate, n-butyl acrylate or 2-ethylhexyl acrylate;
c. from 0 to 50% by weight of aromatic vinyl compounds, such as styrene, methylstyrene or vinyltoluene;
d. from 0 to 20% by weight of other monomers having functional groups, includes acrylic acid, methacrylic acid, crotonic acid, itaconic acid, maleic acid, fumaric acid, maleic anhydride, maleic monoesters, acrylamide, methacrylamide, acrylonitrile or N-methylol(meth) acrylamide and glycidyl(meth)acrylate, provided that the total of components a) and b) must be at least 5% by weight.

The acrylate resins can be prepared by conventional polymerization including bulk, solution, suspension, emulsion or precipitation polymerization, but preferably by bulk polymerization which, in turn, can be initiated by UV light.

Further polymerization initiators which are used are the conventional peroxides or azo compounds, such as dibenzoyl peroxide, tert-butyl perbenzoate or azobisisobutyronitrile. The molecular weight can be regulated using, conventional molecular weight regulator, including the sulphur compounds such as tertdodecanethiol.

Preferred polyethers can be prepared by the polyaddition of an epoxide, such as ethylene oxide, propylene oxide, butylene oxide, trimethylene oxide, 3,3-bis(chlorosethyl) oxacyclobutane, tetrahydrofuran, styrene oxide, the bis(2,5-epoxypropyl) ether of diphenylolpropane or epichlorohydrin with itself, for example in the presence of $BF_3$, or by the addition of the epoxide, if desired alone or as a mixture or in succession, with starting components containing reactive hydrogen atoms, such as alcohols or amines, including water, ethylene glycol, 1,3-propylene glycol or 1,2-propylene glycol, pentamethylene glycol, hexanediol, decamethylene glycol, trimethylolpropane, 4,41-dihydroxydiphenylpropane, aniline, ammonia, ethanolanine, ethylenediamine, di($\beta$-hydroxypropyl)methylamine, di($\beta$-hydroxyethyl)aniline, hydrazine, and also hydroxyalkylated phenols, such as di($\beta$-hydroxyethoxy) resorcinol.

It is also possible to employ polyureas and/or polyurethanes containing hydroxyl groups in the process of the present invention.

As polyhydroxy compounds it is also possible, of course, to employ mixtures of two or more polyhydroxy compounds as described above.

The ratio in which the hydroxyl group-containing polymers and the isocyanate component are mixed is selected such that 0.6–1.2, preferably 0.8–1.1, most preferably 1.0, free and/or blocked NCO groups are present per OH group.

For the production of PUR powder coatings, the isocyanate component is mixed and homogenized in the melt with the appropriate hydroxyl group-containing polymer and, if desired, catalysts, pigments, fillers, levelling agents, such as silicone oil, and acrylate resins. This can be carried out in any suitable apparatus, such as a heatable kneading apparatus, but preferably by extrusion, in which case upper temperature limits of from 130 to 140° C. should not be exceeded. After the extruded composition has been cooled to room temperature and comminuted appropriately, it is ground to give the ready-to-spray powder. The application of the ready-to-spray powder to suitable substrates can be carried out by conventional processes, including, but not limited to, electrostatic powder spraying, fluidized-bed sintering, or electrostatic fluidized-bed sintering. After the application of the powder, the coated work-pieces are heated for curing purposes for from 60 to 10 minutes at a temperature of from 160 to 220° C., preferably for 30 to 10 minutes at from 180 to 210° C.

For the production of solvent-containing, one-component PUR stoving enamels, the isocyanate component can be dissolved in appropriate solvents and homogenized with the hydroxyl group-containing polyesters which are suitable for this area of application, and can be formulated in a known manner with the above-mentioned additives. Solvents suitable for the one-component stoving enamels according to the invention are those whose lower boiling point is about 100° C. The upper limit of the boiling point of the solvent depends on the respective baking temperatures. If baking is carried out at relatively high temperatures, the boiling points of the solvents to be used must be at relatively high temperatures. Suitable solvents include the following: hydrocarbons, such as toluene, xylene, Solvesso® 100, 150 and 200 (mixtures of aromatic compounds from Esso), tetraline, decaline, esters such as, for example, butyl acetate and hexyl acetate, ethylglycol acetate, butylglycol acetate, methoxypropyl acetate (MOP-A) etc., and ketones such as, for example, methyl isobutyl ketone, diisobutyl ketone and isophorone. The solvents mentioned can also be employed as mixtures.

The one-component PUR stoving enamels are suitable, in particular, for application to metal surfaces, but also to articles made from other materials such as glass or plastic. The coating materials according to the invention also find application in coil-coating, for weather-resistant one-coat and two-coat systems. The application of the solvent-containing and optionally pigmented coating system is carried out by knife coating, roller coating, spraying, pouring etc. The curing of the one-component PUR stoving enamels according to the invention is carried out, depending on the application, in a temperature range of from 160 to 350° C., preferably at between 180 and 300° C., in a period of from 30 minutes to 30 seconds. The coated film exhibit outstanding technological properties, especially with regard to flexibility and weather resistance.

Other features of the present invention will become apparent in the course of the following descriptions of exemplary embodiments which are provided for illustrative purposes only and are not intended to be limiting of the present invention, unless otherwise indicated.

EXAMPLES

In these examples the metering of the reaction component is not dealt with in more detail but is carried out using conventional metering pumps and/or belt weighers.

A Preparation of The Process Products According to the Invention

General Preparation Procedure

The uretdione prepared from IPDI was fed into the intake housing of a twin-screw extruder at a temperature from 60 to 110° C., with the diol, the diol mixture or the diol/monoalcohol mixture being metered in simultaneously at a temperature of from 25 to 110° C. The OH component or the uretdione contained, if appropriate, the quantity of catalyst required, based on the end product.

The extruder employed was composed of ten housings which were thermally controlled over five heating zones. The temperatures of the heating zones were regulated as follows: 1st zone 60–180° C., 2nd zone 60–170° C., 3rd zone 60–150° C., 4th zone 80–150° C. and 5th zone 70–150° C.

All of the temperatures represent desired temperatures; temperature regulation in the housings of the kneading apparatus was effected by electrical heating and pneumatic cooling. The die element was heated using an oil thermostat.

The speed of rotation of the twin screw, the entire length of which was composed of conveying elements and kneading elements, was from 50 to 380 rpm. The proportion of the reactants was made such that the OH/NCO ratio was from 1:0.5 to 1:1.5, in general 1:

1. The diol/monoalcohol mixture was proportioned as follows: 1.75:1–2:1.

The reaction product, which was obtained at a rate of from 10 to 180 kg/h, was either cooled and then comminuted or shaped and bagged, or the actual melt was shaped, cooled and bagged.

The physical and chemical characteristics of the examples prepared in this way according to the invention are summarized in Table 1.

The uretdione-polyisocyanates employed had the following characteristics:

IPDI-UD NCO content free: 16.8–18.5% by weight total: 37.0–37.7% by weight

HDI-UD NCO content free: 20–21.5% by weight total: 35.5–37.8% by weight

TABLE 1

Polyaddition products containing uretdione groups

| Example A | Polyisocyanate uretdione | Composition in mol Diol | Monoalcohol | NCO content % by weight free | total | Melting range ° C. | Glass transition temperature ° C. |
|---|---|---|---|---|---|---|---|
| 1 | 3 (IPDI) | 2 B | | 4.4 | 21.9 | 85–89 | 43–58 |
| 2 | 5 (IPDI) | 4 B | | 2.3 | 19.1 | 103–109 | 50–62 |
| 3 | 4 (IPDI) | 5 B | | 0 | 10.9 | 116–118 | 75–100 |
| 4 | 4 (IPDI) | 3 HD | | 3.1 | 19.9 | 76–84 | 47–52 |
| 5 | 4.5 (IPDI) | 3.5 Pm | | 2.5 | 18.8 | 78–83 | 45–51 |
| 6 | 5 (IPDI) | 4 MP | | 2.5 | 19.2 | 100–107 | 52–61 |
| 7 | 4.5 (IPDI) | 3.5 E | | 2.6 | 19.9 | 87–91 | 48–59 |
| 8 | 4.5 (IPDI) | 3.5 Eg | | 2.5 | 16.2 | 85–93 | 47–55 |
| 9 | 4 (IPDI) | 3 DMC | | 2.7 | 18.7 | 89–94 | 51–59 |
| 10 | 4.5 (IPDI) | 3.5 B | 1 EH | 1.1 | 17.9 | 107–114 | 60–69 |
| 11 | 4.5 (IPDI) | 3.5 B | 2 EH | 0.5 | 16.3 | 102–108 | 60–69 |
| 12 | 4 (IPDI) | 3 Eg | 2 M | 0.4 | 14.6 | 86–92 | 49–58 |
| 13 | 4.5 (IPDI) | 3.5 E | 2 EH | 0.4 | 16.6 | 111–121 | 63–74 |
| 14 | 4 (IPDI) | 3 B | 2 M | 0.5 | 16.9 | 95–99 | 57–63 |
| 15 | 4.5 (IPDI) | 3.5 MP | 2 EH | 0.6 | 16.1 | 108–113 | 64–71 |
| 16 | 4.5 (IPDI) | 3.5 B | 2 Et | 0.5 | 16.8 | 108–113 | 63–71 |
| 17 | 4.5 (IPDI) | 3.5 HD | 2 EH | 0.6 | 16.0 | 100–108 | 55–62 |
| 18 | 4.5 (IPDI) | 3.5 B | 2 DBA | 0 | 15.5 | 115–126 | 69–76 |
| 19 | 4 (IPDI) 0.5 (HDI) | 3.5 E | 2 EH | 0.5 | 16.8 | 107–116 | 59–68 |
| 20 | 4 (IPDI) 0.5 (HDI) | 3.5 B | 2 Et | 0.7 | 17.0 | 102–109 | 57–65 |

B. Polyol Component
General Preparation Procedure

The starting components—terephthalic acid (Ts) and/or isophthalic acid (Is) and /or dimethyl terephalate (DMT), hexane-1,6-diol (HD) and/or neopentylglycol (NPG) and/or 1,4-dimethylolcyclohexane (DXC) and/or 2,2,4(2,4,4)-dimethylhexanediol (THH-d) and trimethylolpropane (THP)—were placed in a reactor and heated using an oil bath. After the substances had predominantly melted, 0.05% by weight of di-n-butyltin oxide was added as catalyst at a temperature of 160° C. Initial elimination of methanol occurred at a temperature of about 170° C. The temperature was raised to from 200 to 230° C. over the course of from 6 to 8 h, and the reaction was brought to an end over the course of a further 12 to 15 h. The polyester was cooled to 200° C. and substantially freed from volatile constituents by applying a vacuum (1.33 mbar) over the course of from 30 to 45 min. The bottom product was stirred throughout the reaction period, and a gentle stream of $N_2$ was passed through the reaction mixture.

The table below indicates the polyester compositions and the corresponding physical and chemical characteristics.

TABLE 2

Polyesters

| Example B | Ts mol | DMT mol | Starting components HD mol | NPG mol | DMC mol | TMP mol | OH number mg KOH/g | Acid number mg KOH/g | Melting range ° C. | DTA* ° C. | Visc. at 160° C. mPa · s |
|---|---|---|---|---|---|---|---|---|---|---|---|
| 1 | 10 | 10 | 6.25 | 10.5 | 2 | 2.9 | 55–60 | 3–4 | 75 | 50 | 25 000 |
| 2 | Polyester from Hoechst AG ALFTALAT AN 739 | | | | | | 55–60 | 2–3 | 70 | 50 | 28 000 |
| 3 | 9 IS | 9 | 3 TMH-d. | 13 | 3 | 1 | 52–55 | 2–4 | 73–75 | 50 | 10 000 |
| 4 | 7 | — | 5 | 1 | — | 2 | 105–112 | <2 | — | (−3)–(+9) | — |

C Polyurethane Powder Coatings
General Preparation Procedure

The ground products, crosslinking agents, polyester, levelling agents and, if appropriate, catalyst masterbatch were intimately mixed, together if desired with the white pigment, in an edge runner mill and then homogenized in an extruder at from 80 to 120° C. After the mixture had cooled the extrudate was fractionated and ground to a particle size <100 μm using a pin mill. The powder thus prepared was applied to degreased and optionally pretreated iron panels using an electrostatic powder spraying unit at 60 kV, baked in a circulating air drying cabinet at temperatures of between 180 and 200° C.

The product properties are provided in Tables 3 and 4 below.

The abbreviations in Tables 3–5 below denote:
LT=layer thickness in μm
HIK=König hardness (sec) (DIN 53 157)
BB=Buchholz hardness (DIN 53 153)
Ei=Erichsen indentation (nm) (DIN 53 156)
CH=Crosshatch test (DIN 53 151)GG 20° ∢
GG6° ∢ =measurement of gloss acc. to Gardner (ASTM-D 523)
Imp. rev.=impact reverse in g·m

TABLE 3

Pigmented powder coatings

| Example C Formulation | 1 | 2 | 3 | 4 | 5 | 6 | 7 | 8 *o | 9 | 10 o | 11 | 12 *o |
|---|---|---|---|---|---|---|---|---|---|---|---|---|
| Crosslinking agent acc. to A (Example) | 19.04 (2) | 27.4 (3) | 30.2 (3) | 17.97 (5) | 20.27 (8) | 20.85 (10) | 20.06 (10) | 17.41 (10) | 22.44 (11) | 22.44 (11) | 21.6 (11) | 18.06 (11) |
| Polyester acc. to B 1 | — | — | 69.8 | — | — | 79.15 | — | 82.59 | 77.56 | 77.56 | — | — |
| Polyester acc. to B 2 | 80.96 | — | — | — | — | — | 79.94 | — | — | — | 78.4 | 81.94 |
| Polyester acc. to B 3 | — | 72.6 | — | 82.03 | 79.73 | — | — | — | — | — | — | — |
| Coating data | | | | | | | | | | | | |
| LT | 50–70 | 60–75 | 55–75 | 60–70 | 65–75 | 60–70 | 60–75 | 55–75 | 50–60 | 60–70 | 55–65 | 60–70 |
| HK | 187 | 185 | 186 | 189 | 182 | 183 | 180 | 184 | 187 | 185 | 181 | 183 |
| HB | 100 | 111 | 100 | 100 | 111 | 111 | 111 | 100 | 111 | 125 | 100 | 111 |
| CH | 0 | 0 | 0 | 0 | 0 | 0 | 0 | 0 | 0 | 0 | 0 | 0 |
| GG | 88 | 90 | 86 | 89 | 88 | 89 | 88 | 89 | 90 | 92 | 89 | 87 |
| EI | >10 | >10 | >10 | >10 | >10 | >10 | >10 | >10 | >10 | >10 | >10 | >10 |
| Imp. rev. | 806.4 | >944.6 | >944.6 | >944.6 | 806.4 | 806.4 | >944.6 | >944.6 | >944.6 | >944.6 | 691.2 | 944.6 |

Notes
All formulations contain 40% by weight of TiO$_2$ (white pigment) and in each case 0.5% by weight of levelling agent and benzoin; the OH/NCO ratio is 1:1; o = 0.15% DBTL; *OH/NCO = 1:0.8
Curing conditions: 200° C./15 minutes (with o) or 20 minutes

TABLE 4

Pigmented powder coatings

| Example C Formulation | 13 o | 14 | 15 *o | 16 | 17 o | 18 | 19 o | 20 | 21 | 22 o | 23 | 24 |
|---|---|---|---|---|---|---|---|---|---|---|---|---|
| Crosslinking agent acc. to A (Example) | 21.6 (11) | 22.3 (13) | 18.51 (13) | 21.92 (16) | 21.92 (16) | 21.1 (16) | 21.1 (16) | 22.77 (17) | 21.92 (17) | 21.92 (17) | 21.92 (19) | 19.69 (19) |
| Polyester acc. to B 1 | — | 77.87 | 81.49 | 78.08 | 78.08 | — | — | 77.23 | — | — | 78.08 | — |
| Polyester acc. to B 2 | 78.4 | — | — | — | — | 78.9 | 78.9 | — | 78.08 | 78.08 | — | — |
| Polyester acc. to B 3 | — | — | — | — | — | — | — | — | — | — | — | 80.31 |
| Coating data | | | | | | | | | | | | |
| LT | 60–70 | 50–60 | 60–65 | 70–80 | 60–75 | 70–80 | 60–70 | 50–65 | 55–70 | 60–75 | 70–80 | 60–70 |
| HK | 185 | 185 | 189 | 183 | 179 | 178 | 181 | 178 | 180 | 184 | 177 | 179 |
| HB | 111 | 111 | 111 | 100 | 100 | 100 | 100 | 111 | 100 | 111 | 100 | 100 |
| CH | 0 | 0 | 0 | 0 | 0 | 0 | 0 | 0 | 0 | 0 | 0 | 0 |
| GG | 86 | 89 | 89 | 91 | 90 | 89 | 88 | 93 | 90 | 88 | 88 | 90 |
| EI | >10 | >10 | >10 | >10 | >10 | >10 | >10 | >10 | >10 | >10 | >10 | >10 |
| Imp. rev. | >944.6 | >806.4 | >944.6 | 806.4 | >944.6 | 691.2 | 806.4 | 806.4 | 806.4 | 944.6 | 806.4 | 944.6 |

Notes
All formulations contain 40% by weight of TiO$_2$ (white pigment) and in each case 0.5% by weight of levelling agent and benzoin; the OH/NCO ratio is 1:1; o = 0.15% DBTL *OH/NCO = 1:0.8
Curing conditions: 200° C./15 minutes (with o) or 20 minutes Levelling Agent Masterbatch 10 percent by weight of the levelling agent—a commercially available copolymer of butyl acrylate and 2-ethylhexyl acrylate—was homogenized in the melt in the corresponding polyester and, after solidifying, was comminuted.

Catalyst Masterbatch 5 percent by weight of the catalyst—DBTL—was homogenized in the melt in the corresponding polyester and, after solidifying, was comminuted.

D One-Component Polyurethane Stoving Enamels
Preparation of the Crosslinking Agent Solution 600 parts by weight of the blocked polyisocyanate adducts prepared according to A I or A II were dissolved with stirring in 400 parts by weight of solvent mixture at 50–60° C., and the flow time was determined in a DIN 4 cup at 20° C. or in a rotary viscometer at 25° C.
a) A 12 (MOP-A/Solvesso 100=1:2) 10 500 mpa·s
b) A 3 (MOP-A/Solvesso 100=1:2) 22 000 mpa·s
c) A 14 (MOP-A/Solvesso 100=1:2) 45 500 mpa·s
d) A 11 (MOP-A/Solvesso 100=1:2) 55 000 mpa·s II. Preparation of the Polyester Solution 600 parts by weight of polyester according to B 4 and B 5 were dissolved with stirring in 400 parts by weight of solvent mixture at 80–90° C., and the flow time was determined in a DIN 4 cup at 20° C.

a) B 4 (MOP-A/Solvesso 100=1:2) 410 seconds

III. Preparation of the One-component PUR Stoving Enamels a) Stock Enamel Solution The 60% by weight polyester solution was homogenized with stirring with the calculated quantity of the 60% by weight crosslinking agent solution at 50–60° C., and the flow time was determined in a DIN 4 cup at 20° C.

1) acc. to Example D I a and acc. to Example D II 370 seconds
2) acc. to Example D I b and acc. to Example D II=1 150 seconds
3) acc. to Example D I c and acc. to Example D II=850 seconds
4) acc. to Example D I d and acc. to Example D II=950 seconds b) Pigmented Enamel Solutions The stock enamel solutions prepared according to D III a) were admixed, if necessary, with further solvent mixture—corresponding to the stock solution—and then dispersed with white pigment ($TiO_2$) and with an antifoam and levelling agent customary in PUR chemistry in a stirred ball mill.

These pigmented enamels were applied to degreased and/or pretreated 0.8–1 mm steel and/or aluminum panels; curing was carried out in a circulating-air laboratory drying cabinet; curing temperatures were between 180 and 250° C.; the layer thickness of the enamel films, depending on each application, was between 25 and 50 $\mu$m.

The product properties are provided in Table 5 below.

TABLE 5

| Formulation | Example D III b | | | |
| --- | --- | --- | --- | --- |
| | 1 | 2 | 3 | 4 |
| Crosslinking agent solution acc. to D I a | 21.6 | — | — | — |
| Crosslinking agent solution acc. to D I b | — | 17.7 | — | — |
| Crosslinking agent solution acc. to D I c | — | — | 19.5 | — |
| Crosslinking agent solution D I d | — | — | — | 19.7 |
| Polyester solution acc. to D II | 40.9 | 38.6 | 41.2 | 40.3 |
| Solvent mixture acc. to the enamel solution employed | 7 | 9.7 | 9.7 | 9.9 |
| White pigment ($TiO_2$) | 29.4 | 28.5 | 28.5 | 29.0 |
| Antifoam (Byk-special) | 1.0 | 1.0 | 1.0 | 1.0 |
| Levelling agent (Silicone oil OL) | 0.1 | 0.1 | 0.1 | 0.1 |
| Coating properties | | | | |
| HK | 197 | 207 | 203 | 205 |
| HB | 125 | 125 | 111 | 125 |
| GG 20° ≮ | 71 | 82 | 81 | 79 |
| GG 60° ≮ | 88 | 89 | 90 | 89 |
| EI | 8.3 | 8.6 | 8.0 | 8.1 |
| CH | 0 | 0 | 0 | 0 |
| Pencil hardness | 2H | 2H | 2H | 2H |

Note
Curing 250° C./150 seconds

What is claimed as new and is desired to be secured by Letters Patent of the United States is:

1. A process for the preparation of an adduct containing uretdione, groups, comprising intimately admixing a polyisocyanate-uretdione having at least two free isocyanate groups, a diol and, optionally, a monoalcohol or monoamine or both, wherein said process is a solvent-free and continuous procedure and is performed in an intensive kneading apparatus at a temperature at least as high at which said adduct would unblock in the absence of performing in said intensive kneading apparatus.

2. The process according to claim 1, wherein said intensive kneading apparatus is a single- or multiscrew extruder.

3. The process according to claim 1, wherein said intensive kneading apparatus is a multiscrew extruder and said multiscrew extruder is a twin-screw extruder.

4. The process according to claim 1, wherein said intensive kneading apparatus is operated at a temperature sufficient to provide reaction between said polyisocyanate-uretdione, said diol and, if present, said monoalcohol or monoamine or both.

5. The process according to claim 1, wherein said intensive kneading apparatus is operated at a temperature of up to 190° C.

6. The process according to claim 5, wherein said intensive kneading apparatus is operated at a temperature of up to 180° C.

7. The process according to claim 6, wherein said intensive kneading apparatus is operated at a temperature of up to 170° C.

8. The process according to claim 1, wherein said intensive kneading apparatus provides an intensive, rapid mixing and highly viscous product streams coupled with intensive heat exchange, and provides a uniform flow in a longitudinal direction with an approximately uniform reaction residence time.

9. The process according to claim 1, wherein reaction products and a catalyst are supplied to said intensive kneading apparatus in separate streams.

10. The process according to claim 1, wherein reaction products and a catalyst are supplied to said intensive kneading apparatus in a single stream.

11. The process according to claim 1, wherein said diol, said monoalcohol, if present, said monoamine, if present, a catalyst or a mixture thereof, are combined to form a single stream to said intensive kneading apparatus.

12. The process according to claim 1, wherein said polyisocyanate uretdione and, optionally, conventional additives which are inert to said polyisocyanate uretdione are combined in a single stream to said intensive kneading apparatus.

13. The process according to claim 1, characterized in that the input of the product streams can be made variable in sequence and offset in terms of time.

14. The process according to claim 1, further comprising further reacting the product obtained from said intensive kneading apparatus in an after-reaction zone.

15. The process according to claim 1, further comprising cooling the product from said intensive kneading apparatus to a temperature which is adequate for bag-filling/containerization, pre-impressing the product in preparation for comminution and comminuting said pre-impressed product to a granular form having a particle size which is sufficient for bag-filling/containerization.

16. The process according to claim 15, wherein said product is in the form of a continuous strip.

17. The process according to claim 1, wherein a monoalcohol or monoamine or both are present in admixture with said polyisocyanate-uretdione.

18. The process according to claim 1, wherein no dimerizate of polyisocyanate which is free of uret dione groups is produced.

19. The process according to claim 1, wherein no dimerization catalyst is present.

* * * * *

UNITED STATES PATENT AND TRADEMARK OFFICE
CERTIFICATE OF CORRECTION

PATENT NO. : 6,479,613 B2
DATED : November 12, 2002
INVENTOR(S) : Gras et al.

It is certified that error appears in the above-identified patent and that said Letters Patent is hereby corrected as shown below:

<u>Title page,</u>
Item [45] and the Notice information should read as follows:
-- [45]   Date of Patent:     *Nov. 12, 2002

[*] Notice:   This patent issued on a continued prosecution application filed under 37 CFR 1.53(d), and is subject to the twenty year patent term provisions of 35 U.S.C. 154(a)(2)

Subject to any disclaimer, the term of this patent is extended or adjusted under 35 U.S.C. 154(b) by 0 days. --

Item [73], should read as follows:
-- [73] Assignee: Degussa-Huels Aktiengesellschaft, Frankfurt (DE) --

Signed and Sealed this

First Day of April, 2003

JAMES E. ROGAN
*Director of the United States Patent and Trademark Office*